Figure 4:
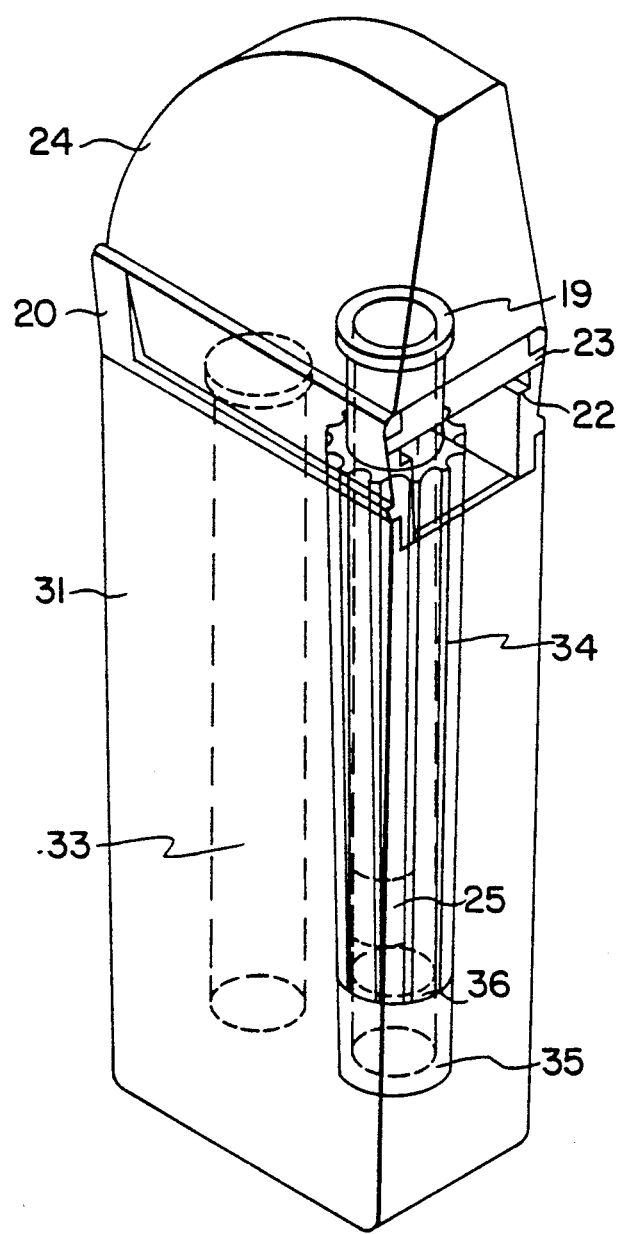

United States Patent [19]
Brodt et al.

[11] Patent Number: 5,055,258
[45] Date of Patent: Oct. 8, 1991

[54] DEVICE FOR ASCERTAINING THE PRESENCE OF AN ANTIGEN OR OF AN ANTIBODY IN A LIQUID SAMPLE

[75] Inventors: Rainer Brodt, Heidenrod-Kemel; Günther Gorka, Idstein; Peter Fehse, Dietzenbach, all of Fed. Rep. of Germany; John Reid; Steve Holmes, both of Clare, Ireland

[73] Assignee: Flemming GmbH, Taunusstein, Fed. Rep. of Germany

[21] Appl. No.: 345,546

[22] PCT Filed: Aug. 13, 1988

[86] PCT No.: PCT/DE88/00495

§ 371 Date: Jun. 16, 1989

§ 102(e) Date: Jun. 16, 1989

[87] PCT Pub. No.: WO89/01626

PCT Pub. Date: Feb. 23, 1989

[30] Foreign Application Priority Data

Aug. 19, 1987 [DE] Fed. Rep. of Germany ....... 3727590
Aug. 5, 1988 [DE] Fed. Rep. of Germany ... 8810037[U]

[51] Int. Cl.$^5$ ..................... G01N 30/00; G01N 21/03
[52] U.S. Cl. ..................... 422/61; 436/165; 436/808; 436/810; 435/975
[58] Field of Search ............... 436/514, 528, 531, 518, 436/535, 541, 810, 510, 807, 808, 165; 435/7, 291, 292, 924, 294, 810, 970, 975; 422/68.1, 69, 101, 102, 58, 59, 60, 61; D24/51, 54, 56

[56] References Cited

U.S. PATENT DOCUMENTS

| 2,587,221 | 2/1952 | Richardson et al. | 23/230 |
| 3,888,629 | 6/1975 | Bagshawe | 23/230 B |
| 4,305,924 | 12/1981 | Piasio et al. | 436/810 |
| 4,315,890 | 2/1982 | Tamers | 422/59 |
| 4,366,241 | 12/1982 | Tom et al. | 435/7 |
| 4,624,929 | 11/1986 | Ullman | 436/179 |
| 4,632,901 | 12/1986 | Valkirs et al. | 435/5 |
| 4,727,019 | 2/1988 | Valkirs et al. | 435/5 |
| 4,740,468 | 4/1988 | Weng et al. | 435/7 |
| 4,742,011 | 5/1988 | Blake et al. | 436/510 |
| 4,797,260 | 1/1989 | Parker | 422/101 |
| 4,912,034 | 3/1990 | Kalra et al. | 435/7 |
| 4,916,056 | 4/1990 | Brown, III et al. | 435/7 |
| 4,920,046 | 4/1990 | McFarland et al. | 435/7 |

FOREIGN PATENT DOCUMENTS

| 0258963 | 3/1988 | European Pat. Off. | 435/7 |
| 0260965 | 3/1988 | European Pat. Off. | 435/7 |

Primary Examiner—David L. Lacey
Assistant Examiner—Jan M. Ludlow
Attorney, Agent, or Firm—Howard M. Ellis; Michael L. Dunn

[57] ABSTRACT

A device for performing immunoassays which has an external housing, a sample container provided with reagents that can be inserted into the external housing, a material container for an absorbent material and membrane-bound antibody or antigen that can be inserted into the sample container, a holder for the material container that can be mounted on the external container, and a spacer that can join the holder and the sample container. When the spacer is in place, the absorbent material is held above the portion of the sample container that holds the sample and when the spacer is removed, the absorbent material is lowered into the sample-containing portion of the sample container. The external housing may also include a container for developer.

7 Claims, 4 Drawing Sheets

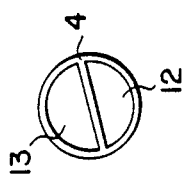
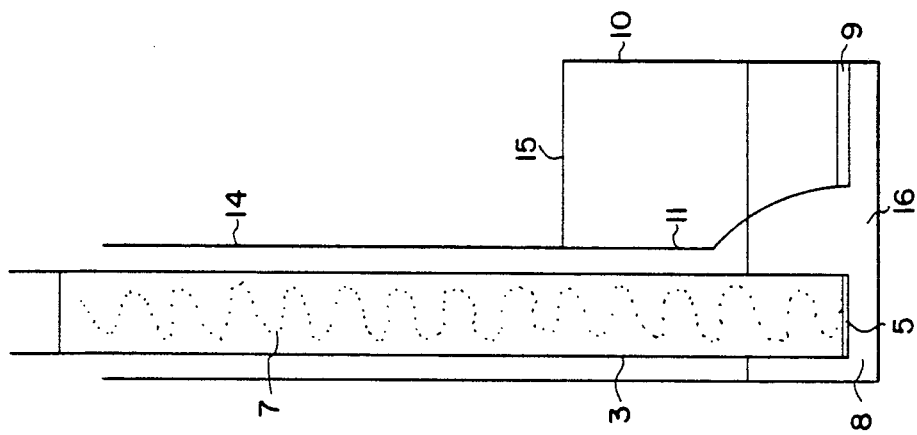
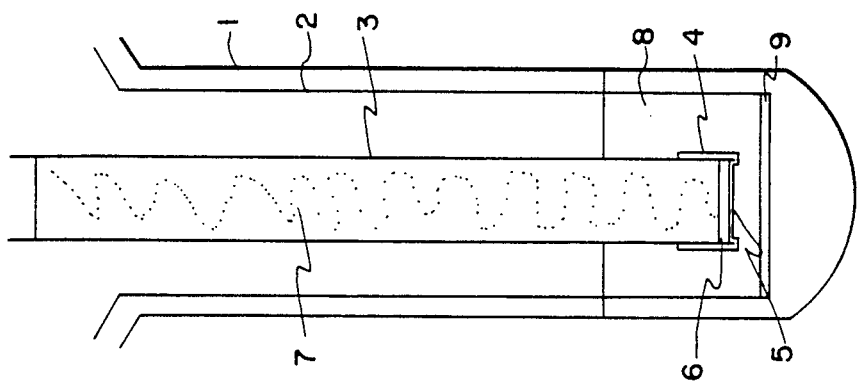

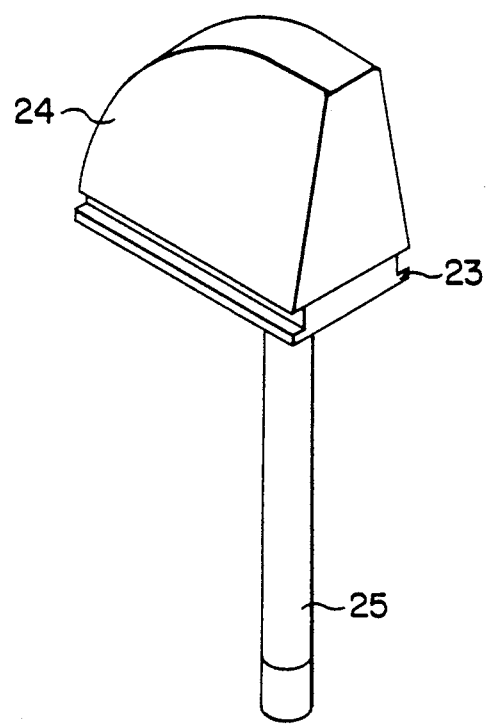
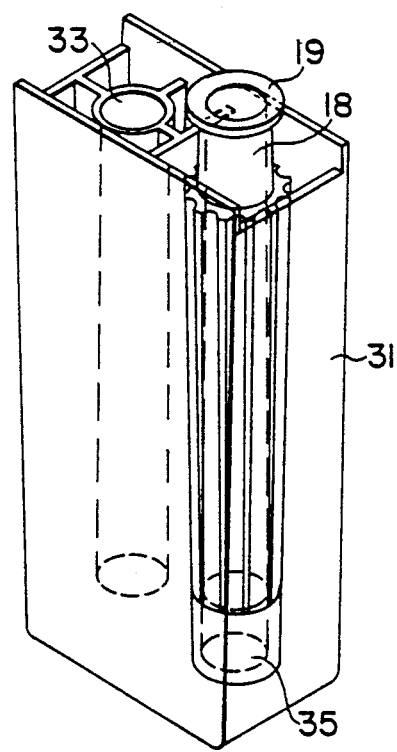
FIG.5

DEVICE FOR ASCERTAINING THE PRESENCE OF AN ANTIGEN OR OF AN ANTIBODY IN A LIQUID SAMPLE

A number of methods are known for ascertaining the presence of an antigen in a liquid sample, in which a solid body, on the surface of which is fixed an antibody which specifically binds the antigen, is dipped into the liquid sample and is furthermore treated with a conjugated antibody which is either directly labelled with a dye or is conjugated with an enzyme which forms a dye in a secondary reaction. If the antigen sought is present in the liquid sample, then it is bonded to the antibody fixed on the solid body, while the conjugated or labelled other antibody which is present in excess is bonded on the antigen. In this way, there is a fixing or formation of dye on the solid body if the desired antigen is present in the sample; otherwise not.

Also, various devices are known for ascertaining the presence of an antigen in a liquid sample, as disclosed for instance in U.S. Pat. No. 4,632,901. This device consists of a cylinder filled with a porous absorbent material above which there is at the top end of the cylinder an adjacent transverse membrane above which there is a funnel part. The corresponding antibody which is intended to bind the antigen is itself bound on the membrane.

When this device is used, the sample to be investigated is poured into the funnel part and is drawn through the membrane by the absorbent material, any antigen which it contains being bonded on the antibody which is fixed on the membrane.

Such a device is certainly suitable for laboratory use since a specific volume of the sample to be investigated has to be introduced by pipette into the funnel part, because the investigated volume of sample must not be too large nor may it be too small. Such a measurement of volume or the use of a pipette is hardly feasible in domestic use, for example for pregnancy testing, since most people are unaccustomed to the use of equipment such as pipettes, so that such methods and devices entail too high a risk of error.

For home use, the carrying out of the test must be as simple and reliable as possible without any possibility of error.

The problem on which the invention is based therefore resided in providing a method of and a device for ascertaining the presence of an antigen or of an antibody in a liquid sample, the said method being capable of being carried out particularly easily and reliably and being virtually foolproof when performed by unskilled persons. In particular, the method was intended to avoid the application of liquid by pipette and also of avoiding any other measurement of volume. Preferably, even the transfusion of the test solution such as urine, should be avoided.

The method according to the invention for ascertaining the presence of an antigen or an antibody in a liquid sample, in which the sample is brought in contact with a porous membrane on which a corresponding antibody or corresponding antigen is bonded and adjacent to which there is a porous absorbent material which absorbs a liquid, and a conjugated or labelled antibody binding on the antigen or antibody, the said antibody possibly being developed to form a dye, is characterised in that there is introduced into a container such a volume of the liquid sample as will only partially fill the pore volume of the absorbent material, after which the membrane with the absorbent material adjacent to it is so dipped into the liquid sample that the latter is substantially completely or in a predetermined volume sucked into the absorbent material by the membrane and against the force of gravity, a final stage possibly being—once the membrane has been removed from the sample—to dip it in a developer solution and allow this latter to be sucked into the absorbent material against the force of gravity.

The conjugated or labelled antibody can be drawn through the membrane together with or after the liquid sample. To this end, it is either contained in the liquid sample while this is being drawn in or is disposed in a separate solution which is sucked in after the liquid sample.

It is essential that the volume of absorbent and the volume of liquid sample which is to be absorbed should be so attuned to each other that while the liquid sample is being sucked in, the pores of the absorbent material are only partially filled. The reason is that the absorbent material must retain sufficient suction power for the desired volume of liquid sample to be sucked into it. This would not be the case if the pores were to be prematurely filled with liquid. Furthermore, the absorbent material has possibly to retain sufficient suction capacity for the subsequent absorption of the solution of conjugated or labelled antibody or developer solution.

Therefore, the method according to the invention can be used to ascertain the presence of both antigens and also antibodies in the liquid sample. In the former case, there is bonded to the membrane an antibody on which the antigen sought is bonded and to which in turn the conjugated or labelled second antibody is bonded. In the latter case, there is bonded to the membrane an antigen on which the antibody sought becomes bonded. The conjugated or labelled second antibody then in turn becomes bonded on the first antibody which is bonded on the antigen.

Preferably, the conjugated antibody used is an antibody conjugated with a dye-forming agent, such as an enzyme which forms a dye in a secondary reaction or a group which forms a dye by subsequent oxidation or reduction. By avoiding an antibody labelled directly with dye, it is possible to ensure that in the secondary reaction or development, dye is only formed when the conjugated antibody is bonded to the membrane via the antigen and the fixed antibody or via the first antibody and the fixed antigen, dye not being absorbed on the membrane by any other means, which might falsify the results.

The secondary reaction or development of the dye is just as simple as binding the antigen on the membrane and simply calls for dipping the membrane with the adjacent absorbent material into the developer solution. At the same time, the absorbent material should still have sufficient free pores to be able to draw the developer solution through the membrane, which means that in the first working stage, only a part of the pore volume of the absorbent material can be filled with the liquid sample.

Generally, it might well be expedient, between drawing in the liquid sample to fix the antigen via the first antibody or to fix the first antibody via the antigen on the membrane and prior to drawing in the developer solution, to rinse off the membrane any excess sample material and/or conjugated or labelled antibody. This can be done for instance under running water or by dipping the membrane into and drawing up rinsing water.

Furthermore, it is expedient to filter the liquid specimen prior to its being sucked up through the membrane, in order to remove any solid constituents which might clog the pores of the membrane.

In the present method, it is important to a certain extent to predetermine the volume of the sample in order on the one hand to avoid the entire pore volume of the absorbent material being filled with the sample and in order on the other to avoid sucking up too small a pore volume, since this would normally result in too little antigen or antibody being bonded on the membrane, resulting in an inadequate colour reaction.

The method according to the invention is extremely simple to perform and virtually eliminates any risk of error even for unskilled persons.

Without any possibility of error, a specific volume of fluid is measured into a small measuring beaker which should be filled to the brim and which is of the type which is for example held in the urine stream for a pregnancy test, whereupon the fluid is transferred to a specimen container in which the test is carried out. Instead of this, the specimen container can also itself be constructed as a measuring beaker and be held in the urine stream. It is then unnecessary to tip the fluid out of the measuring beaker into the specimen container, which itself entails a possible source of error due to shaking.

In both cases, then, the absorbent material container with the membrane at the end is dipped into the specimen container whereupon the specimen solution is sucked through the membrane into the absorbent material. When a specific volume of the specimen or preferably substantially the entire specimen has been drawn in by suction, the absorbent material container is taken out, possibly rinsed and then possibly dipped into the developer solution. After a certain period, the absorbent material container is taken out and the membrane examined visually to establish any colour reaction.

If mention has been made here of a predetermined volume of liquid sample, then this does not need to be exactly observed but can fluctuate for example by 20 or 30% without adversely affecting the qualitative result.

The simplicity and reliability of the way the test is conducted makes it possible for the method and the device according to the invention to be used in the home. The advantages are as follows: there is no need for the specimen fluid to be transferred by pipette. It is unnecessary to pour the specimen fluid into a funnel and onto the membrane which would entail the risk of the fluid being shaken. Simple dipping of the membrane produces an automatic passage of the sample through the membrane without the risk of shaking. Even if the test is stopped, possibly by the test subject being called away by a telephone call or the like, the membrane does not dry out which would be damaging to the result, as is possible for instance in the case of devices according to U.S. Pat. No. 4,632,901.

The small surface area of the membrane and the comparatively large through-flow volume make for a potentially high sensitivity level. By reason of the small membrane area, the costs of the reagents are minimal since only a little first antibody requires to be fixed on the membrane.

It should also be noted that the second conjugated or labelled antibody is present in excess compared with the first antibody or the antigen which is to be bonded thereon, and is accommodated in the specimen container so that the second conjugated or labelled antibody blends with the specimen as it is poured in.

According to a particularly expedient embodiment, the membrane used according to the invention is at the same time provided with a monitoring facility by means of which it can be established simultaneously whether the test is proceeding as desired or has become useless due to over-lengthy storage or such like. For this, the first antibody or the antigen is only bonded to a part of the membrane while on another part either the specific antigen or another antibody is fixed which binds the second conjugated or labelled antibody. If the test is still proceeding properly, then in either case the conjugated or labelled second antibody which is present in excess in the specimen will be bonded. If it is not an antigen but an antibody other than the second antibody which is fixed for bonding of the second antibody, then this fixing can take place directly via the second antibody or via the enzyme which is bonded to it.

The device used for the method according to the invention likewise differs substantially from other devices used according to the state of the art. The device according to the invention, with a porous membrane part on which is bonded an antibody which becomes bonded to the antigen, and a column of a porous absorbent material which is adjacent the membrane part is characterised by a specimen container and a tubular absorbent material container, the latter being sealed off at one end by the membrane part and being open at the other end, specimen container and absorbent material container being so dimensioned that the absorbent material container with the membrane at the bottom can be dipped into the specimen container.

In the case of this device, if a membrane is used which is separated from the absorbent material, then by virtue of its small thickness and flexibility, such a membrane runs the risk of being bent outwardly when the absorbent material is pressed into it. Therefore, it is expedient for a porous rigid supporting member to be disposed between the absorbent material and the membrane. The absorbent material can thereby be in lumps or may consist of a one-piece column.

It is preferable for the absorbent material to consist of a column and to be integrally connected to the membrane part. Such absorbent materials consist for instance of a porous rod of synthetic plastics material connected at one end so that it is integral with a porous membrane consisting of a cellulose material or the like.

What is essential is that the absorbent material be enclosed by a casing which is impervious to liquids, which ensures that fluid is drawn into the absorbent material only through the membrane. It can be a tubular metal container or a synthetic plastics skin which is impervious to liquids and which encloses the column of absorbent material.

Particularly in the latter case, the tubular absorbent material container can also be marketed in the form of several such containers which are connected to one another and which can be torn off or broken away individually as required and to this end, it is expedient to provide between the individual connected absorbent material containers breaking lines or lines of weakness which permit of easy tear-off, possibly by bending the desired unit over sideways.

In the case of another embodiment of the invention, a plurality of absorbent material containers can also be rigidly connected to one another, possibly so that series of tests can be carried out, for instance in laboratories or medical practices. These multiple containers can for example be used in conjunction with dilution test plates, the depressions in the dilution test plates serving as specimen containers. With such a device, it is possible simultaneously to perform several tests at once, since the connected absorbent material containers are dipped simultaneously in several depressions in the dilution test plates.

Since it is expedient, in order to avoid clogging of the membrane pores, to remove any solid particles from the sample before it comes in contact with the membrane, it is preferred to interpose a filter in front of the membrane part in the direction of flow of the sample and against the force of gravity. Such a filter may be a filter plate disposed immediately in front of the membrane and fixed on the absorbent material container. However, the filter can also be so incorporated into the sample container at some suitable location that the entire liquid sample has to pass through the filter before it reaches the membrane.

A preferred device according to the invention comprises an external container, a specimen container which can be inserted into the external container, a tubular absorbent material container closed at one end by the membrane part and provided at the other end with an aperture and which can be inserted into the specimen container, being fixed on a holding part which can be placed on the external container, and also comprising a removable spacer which can be mounted on the external container to engage into the holding part and an extension of the specimen container, the said removable spacer separably connecting the extension of the specimen container to the holding part, the dimensions of the external container, spacer and absorbent material container being such that when the spacer is fitted, the membrane part is above the specimen container and when the spacer is removed, the said membrane part is in the specimen container.

Preferably, the spacer is laterally removable and for this purpose it is substantially U-shaped, having a first groove or tongue which engages a tongue or groove on the holding part and having a second groove or tongue engaging a tongue or groove on the top area of the extension of the specimen container. In this respect, a tongue engaging a groove may be constructed in various ways such as for example in the form of a rib which substantially completely fills the groove or in the form of individual projections which may for example be disposed in a punctiform arrangement on a line engaging the groove.

The spacer is separably connected to the extension of the specimen container in a simple manner in that the latter comprises at its upper end a bead which forms the tongue and which can be pushed into a groove in the preferably U-shaped spacer. Conversely, it is naturally also possible for the spacer to comprise a rib which can engage a groove at the upper end of the extension of the specimen container. The same effect can also be achieved if the extension of the specimen container has at its upper end a bead which rests on a shoulder on the inside of the spacer.

What is essential in all these possible embodiments is that when the spacer is fitted, the holding part is connected to the speciment container via the extension thereof, whereas when the holding part is removed, this connection is automatically broken, so that when the holding part is removed from the external container the specimen container is left in the external container.

The specimen container and its extension may be constructed in various ways. It is expedient for the extension of the specimen container to be of substantially tubular construction. The specimen container itself is then ideally an end portion of the tubular extension which is beaker-shaped, i.e. closed at the bottom end, being provided at a certain distance from the bottom of the beaker shape with lateral fluid inlet apertures. These lateral fluid inlet apertures are a way of determining the level of fluid in the specimen container since when the fluid is introduced at the side, the specimen container only fills as far as these lateral fluid inlet apertures. This ensures that the specimen container only accommodates a predetermined quantity of fluid.

The holding part which is intended to remove the specimen container from the external container when it is connected to it via the spacer, is preferably constructed as a cover which closes off the external container so that while the device is standing, it can for instance prevent foreign substances falling into it. In itself, it is sufficient that the holding part and the spacer can in some way be mounted on the external container. It is however expedient if the bottom edge of the holding part and of the spacer is so constructed that either part can alternatively fit onto the aperture of the external container.

The device according to the innovation functions in the following way:

To start with, the device is so assembled that when the spacer is fitted, it is disposed between the external container and the holding part, with the result that the specimen container is connected to the holding part and can be withdrawn from the external container together with the holding part.

When the device is used for a test, the holding part with the specimen container fixed to it via the spacer is removed from the external container, whereupon the apertures in the specimen container are held in the stream of urine until the specimen is filled to the predetermined level with urine.

To this end, it is expedient for the tubular extension of the specimen container to have longitudinally extending run-off ribs on its periphery, between the lateral fluid inlet apertures. This facilitates reliable functioning of the device. In fact, when the tubular extension of the specimen container on which the run-off ribs are provided is held in the stream of urine, the urine runs along the channels formed between the run-off ribs and automatically flows into the lateral fluid inlet apertures until the level of fluid reaches these fluid inlet apertures, which then act as overflows.

The device is put together in such a way that the tubular absorbent material container which is fixed on the holding part is inserted in the tubular extension of the specimen container. In the condition described, with the spacer fitted, however, the bottom end of the absorbent material container, i.e. the membrane part, is above the specimen container or in other words it is above the lateral fluid inlet apertures and therefore, while in this condition, it does not dip into the urine in the specimen container.

When the specimen container is filled with urine, the spacer with the extension of the specimen container fixed to it and with the holding part fixed to it, is again mounted on the external container. The spacer is then removed, i.e. in the preferred U-shaped embodiment it is pulled off sideways. When this happens, the extension of the specimen container is separated from the holding part and at the same time the absorbent material container with the holding part fixed to it slips across the gap left by the spacer and moves more deeply into the extension of the specimen container until the membrane is disposed inside the specimen container.

In this condition, by reason of the suction effect of the absorbent material in the absorbent material container, the urine specimen in the specimen container is sucked through the membrane part into the absorbent material, the desired antigen in the specimen of urine becoming bound to the antibody bonded to the membrane part or the desired antibody in the urine sample is bonded to the antigen which is bound to the membrane part.

For a secondary reaction or development of the dye, it is preferable for the external container to contain, in addition to the above-described parts, a developer container into which the absorbent material container can be inserted. The developer container may be a section of the external container or may for example be a tubular internal container fixed on the external container and which is so dimensioned that it can accommodate the absorbent material container.

Upon completion of the above-described step, the next stage in the test, after the urine specimen has been drawn through the membrane part by a suction effect into the absorbent material container, is for the holding part with the absorbent material container fixed to it to be removed and so rotated that the absorbent material container is dipped into the developer container. After the period of immersion required for the secondary reaction or development, the absorbent material container is removed from the developer container by means of the holding part whereupon it is established visually whether a dye has been formed on the membrane part and now indicates a positive test result.

Figure 6:
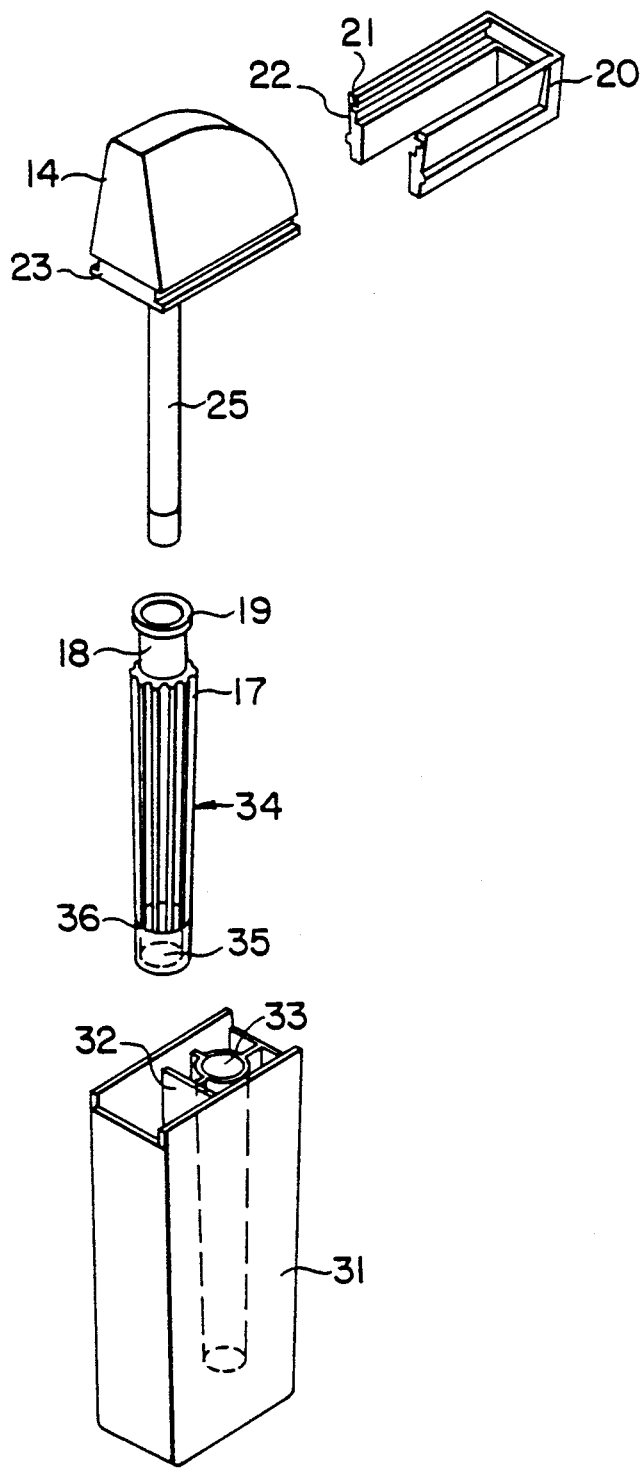

The invention is explained in greater detail in the accompanying drawings, in which:

FIG. 1 is a vertical section through a first embodiment of a device according to the invention, FIG. 2 is a vertical section through a second embodiment of a device according to the invention, FIG. 3 is a plan view of a preferred embodiment of an absorbent material container, viewed from below, FIG. 4 is a perspective view of an embodiment of a device according to the invention in the assembled state and with the spacer fitted, FIG. 5 is a perspective view of the embodiment shown in FIG. 4, after removal of the spacer and with the absorbent material container withdrawn and FIG. 6 is an exploded view of the device shown in FIGS. 4 and 5 with the various individual components in a perspective view.

The embodiment of a device according to the invention which is shown in FIG. 1 comprises a specimen container 1 substantially in the form of a test tube. Inserted concentrically into this is a second container 2 which is closed at the bottom end by a filter 9. Inserted into the container 2 is the absorbent material container 3 which is filled with absorbent material 7. The bottom end of the absorbent material 3 is closed by a cap 4 which supports a membrane 5. Between the membrane 5 and the absorbent material 7 there is a porous rigid supporting part 6.

When the test device according to FIG. 1 is used, firstly, prior to inserting the container 2 and the absorbent material container 3, specimen fluid 8 is poured in by means of a small measuring beaker. Then the container 2 with the filter 9 at the bottom end is inserted, the specimen fluid being forced through the filter 9 into the container 2. Then, the absorbent material container 3 is inserted with the cap 4 downwards. Thereupon, fluid 8 is automatically sucked through the membrane 5 and into the absorbent material 7. When the fluid 8 has been sucked in to the level of the filter 5, there is still sufficient capacity left in the pore volume of the absorbent material 7 that upon transfer of the absorbent material container 3 into a developer fluid, a sufficient quantity can still be drawn from the developer fluid into the absorbent material.

The embodiment of a device according to the invention which is shown in FIG. 2 is preferred, since it requires no additional measuring beaker and no transfer of specimen fluid.

The specimen container 10 shown in FIG. 2 comprises a tubular neck 14 which is used at the same time as a handle for holding the specimen container 10 with the aperture 15 positioned in the stream of urine. The specimen container 10 overflows when the space between the aperture 15 and the filter 9, the outside wall and the separating wall 11 is filled with specimen fluid. This space as defined therefore limits the volume of specimen fluid which is desired for the test.

When left to stand briefly, the specimen fluid then flows sufficiently through the filter 9 into the space 16 for the fluid 8 to reach the level indicated in the drawing.

Then, the absorbent material container 3 with the membrane 5 downwards is inserted into the tubular neck 14 whereupon the fluid is sucked into the absorbent material 7 to the level of the membrane.

In the case of the preferred embodiment shown in FIG. 2, the absorbent material 7 consists of a synthetic plastics column permeated by pores connected at its bottom end to and in one piece with the membrane 5, being enclosed by a skin of material which is impervious to liquids.

FIG. 3 shows a preferred embodiment of the cap 4 of the absorbent material container shown in FIG. 1. This cap comprises, separate from each other, two inlet apertures above the membrane, the membrane part 12 carrying the fixed antibody which is specific for the antigen which is sought, while the membrane part 13 carries a fixed antigen or an antibody other than the conjugated or labelled second antibody, both the antigen and also the other antibody being capable of binding the second antibody. This part 13 of the membrane serves as a means of checking that the test is properly functioning.

It goes without saying that the specimen container 1 or 10 is marketed already containing the conjugated or labelled second antibody so that when the sample is poured in, this second antibody mixed with the test fluid automatically or possibly after being briefly shaken.

The device shown in FIGS. 4 to 6 consists of an external container 31 with two compartments separated from each other by a separating wall 32 and of which one is empty while the other contains fixed therein a developer container 33 in the form of a tube which is closed at the bottom. Furthermore, the device contains a part 34 which has at the bottom end the beaker-shaped specimen container 35 with a ring of lateral fluid inlet apertures 36 between run-off ribs 17 which extend in the longitudinal direction of the extension 18 adjacent the specimen container 35. At the top end, the extension 18 has an annular bead 19 which can be pushed over a shoulder on the spacer 20.

The spacer 20 is substantially U-shaped and its bottom end fits the aperture in the external container 31. In the upper portion, the spacer 20 has on both inside faces grooves 21 into which it is possible to insert the ribs 23 on both sides of the holding member 24. In addition, the spacer 20 has below the grooves 21 respective shoulders 22 over which it is possible to push the annular bead 19 on the extension 18.

The absorbent material container 25 is fixed on the holding part 24 and is closed at the bottom end by a permeable membrane while at the top end, not shown, it comprises venting orifices; it is also filled with an absorbent material.

FIG. 4 shows the device in the initial fitted-together condition in which the U-shaped spacer 20 is pushed between the holding part 24 and the external container 31, a tongue-and-groove joint fixing the holding part while the specimen container is in itself fixed by the fact that the annular bead 19 on the extension 18 is resting on the shoulder 22. In this condition, the bottom end of the absorbent material container 25 with the membrane part is above the ring of fluid inlet apertures 36 and therefore above the specimen container 35. In this condition, therefore, the holding part 24 together with the spacer 20 and the specimen container 5 and its extension 18 can be detached from the external container 31 in order to hold the specimen container in the stream of urine.

As FIG. 5 shows, removal of the spacer 20 results in the extension 18 on the specimen container 35 becoming detached and upon removal of the holding part 24 it remains in the external container 31 with the absorbent material container 25. When the holding part 24 is fitted on the top edge of the external container 31, the bottom end of the absorbent material container 25, with the membrane part, slips into the specimen container 35 and can therefore draw through the membrane by a suction effect the urine sample which is contained in the specimen container 35.

Afterwards, the holding part as shown in FIG. 6, is once again removed, rotated through 180° and then dipped in the developer container 33 in that the holding part is fitted on the external container 31 in the opposite direction. When the developing time has elapsed, the holding part 24 with the absorbent material container 25 fixed to it, is withdrawn from the developer container 33 and the result of the test is ascertained visually by looking at the membrane part.

EXAMPLE 1

0.2 ml of urine are introduced by pipette into a circular vessel the inside diameter of which is 2 mm larger than the outside diameter of the absorbent material container, the urine becoming blended with a second antibody against HCG (human-chlorion-gonadotropin), labelled with alkaline phosphatase and containing respectively 0.50, 100, 200, i.u. HCG/1. Placed in front of the absorbent material is a membrane with a pore size of $3\mu$, which has been coated with the first antibody against HCG over one half and with HCG over the other half.

The absorbent material container (outside diameter 11 mm) is immersed in the urine and left in it until the entire volume has been sucked through (approx. 30 seconds). Afterwards, the absorbent material container is transferred to a second circular vessel which contains a solution of 3 mmole/1 indoxyl phosphate in 1 m. diethanolamine, pH 9.8 (0.5 ml).

The absorbent material container is likewise left in this until the entire volume of the second solution, which serves at the same time as a washing solution, and as a substrate for alkaline phosphatase, has been sucked through the membrane (taking approx. 1 minute).

The following results were obtained:

The half of the membrane which is coated with HCG, once the absorbent container has been removed from the second vessel, shows a dark blue discolouration for any urine solution used in the experiment. The other half which is coated with an antibody against HCG, when exposed to the urine which does not contain any HCG, shows a white background which in course of time becomes discoloured to a slight bluish shade, while in the case of urines which contain HCG, a marked discolouration is visible which becomes more intensively blue as the concentration increases.

By washing the membrane briefly in running mains water (for 5 to 10 seconds) directly after removal from the second solution, the light blue discolouration which resulted in the case of a urine with no HCG is prevented.

EXAMPLE 2

The test is carried out in a manner similar to that in Example 1 with the difference that firstly the urine (0.2 ml) is drawn up after which, in a second vessel, the labelled antibody is drawn up (0.2 ml) and then the substrate and washing solution is drawn up (0.5 ml). The results are identical, the modus operandi given in this example having the advantage that a positive result is also obtained with very high HCG concentrations (above 200,000 i.u. HCG/1) without having to use very large quantities of second antibody.

EXAMPLE 3

The test is conducted in a manner similar to that in Example 1, the first antibody and the HCG being applied crosswise to the membrane so that the first antibody represents one bar while HCG represents the other bar of the cross. With this configuration, urines which do not contain HCG result in one bar being coloured blue, namely that consisting of HCG, which has to be interpreted as negative or minus, while with urines which contain HCG, both bars show a blue discolouration, which is clearly evidence of a positive or plus result. Actually in home use, this version must be regarded as advantageous since it can be easily and clearly read.

EXAMPLE 4

The test is conducted in a manner similar to that in Example 2, a part of the membrane being coated with rubella[(4)] antigen while another part is coated with rabbit antibodies, directed against IgG (immunoglubin G) from sheep. Initially, human sera (0.2 ml) are applied to a specimen container by pipette after which the absorbent container is dipped into the specimens until the total quantity of the serum has been drawn through (approx. 1 min). Then the absorbent containers are transferred to a second vessel which contains antibodies from sheep (0.2 ml), directed against human IgG and labelled with alkaline phosphatase. The total quantity is drawn through (approx. 1 min), followed by transfer to a third vessel which contains buffered cooking salt solution (0.9%) with 0.2% Tween 20 (non-ionic detergent, brand name) (0.5 ml, taking about 90 sec).

Then, in a fourth vessel, substrate solution is sucked through (0.5 ml, takes about 2 min).

The discolouration which results can then be stabilised either by rinsing with mains water as described in Example 1 or by transfer to a further vessel which again contains buffered cooking salt solution with 0.2% tween 20.

All sera show in the area coated with rabbit antibody directed against sheep IgG a blue discolouration which can be regulated by the quantity of rabbit antibody applied and which was so adjusted that the resultant blue discolouration corresponds to the quantity of antibodies in the human sera, which occurs in the area coated with rubella antigen when the human serum comprises sufficient immunity to rubella (as a rule a titre of 1:8 to 1:16 in the haema-agglutination inhibiting test, which serves as the reference method).

By comparing the two areas, it is easy to establish whether that which is under test does not show sufficient immunity (blue discolouration in the rubella coated zone less than in the zone coated with rabbit antibodies) or whether immunity is actually present (blue discolouration of equal strength or stronger).

It will be readily seen that tests of this type can be applied to many and varied antigens and antibodies.

We claim:

1. A device for determining the presence of an antigen or antibody in a liquid sample, which comprises external container means; liquid sample container means dimensioned for insertion into said external container means; reagent means disposed in said liquid sample container means; material container means and a porous absorbent material disposed therein, said material container means dimensioned for insertion into said liquid sample container means, said material container means having a porous membrane mounted on a lower end thereof, said porous membrane comprising bound antibody or antigen; holding means for said material container means, said holding means being constructed so as to be mounted on said external container means; spacer means for connecting said liquid sample container means to said holding means, the dimensions of said external container means, spacer means and material container means being such that when said spacer means is mounted between said holding means and said liquid sample container means said porous membrane is at a higher level relative to a liquid sample in said liquid sample container means and when said spacer means is removed the membrane is disposed at a lower level such that a liquid sample in the liquid sample container means is drawn through said membrane into said absorbent material.

2. The device of claim 1, wherein the reagent comprises a conjugated or labelled antibody.

3. The device of claim 1 wherein the spacer means is of substantially U-shaped construction and has a first groove or tongue and a second groove or tongue; the holding means has a tongue or groove for engaging, respectively, the first groove or tongue of the spacer means; and an upper portion of the liquid sample container means has a tongue or groove for engaging, respectively, the second groove or tongue of the spacer means.

4. The device of claim 3 wherein the second groove or tongue of the spacer means is a groove in the form of shoulder and the tongue or groove of the upper portion of the liquid sample container means is a tongue in the form of a bead on an upper edge of the liquid sample container means.

5. The device of claim 1 wherein the external container means includes a container containing a developer into which the container means containing said absorbent material can be inserted.

6. The device of claim 5 wherein the liquid sample container means comprises a tubular extension, an end portion of said tubular extension which is substantially beaker-shaped at the bottom and further comprises lateral fluid inlet apertures.

7. The device of claim 6 wherein the tubular extension comprises longitudinal run-off ribs between the lateral fluid inlet apertures.

* * * * *